United States Patent
Montalto et al.

(10) Patent No.: US 6,743,899 B2
(45) Date of Patent: Jun. 1, 2004

(54) PROCESS FOR INACTIVATING PRIONS IN LIPOPROTEINS

(75) Inventors: Joseph G. Montalto, Bradley, IL (US); Thomas M. McCall, Bourbonnais, IL (US); Judith A. Vollmer-Gash, Kankakee, IL (US)

(73) Assignee: Serologicals Royalty Company, Norcross, GA (US)

( * ) Notice: Subject to any disclaimer, the term of this patent is extended or adjusted under 35 U.S.C. 154(b) by 0 days.

(21) Appl. No.: 09/974,497

(22) Filed: Oct. 9, 2001

(65) Prior Publication Data

US 2003/0032780 A1 Feb. 13, 2003

Related U.S. Application Data

(60) Provisional application No. 60/289,637, filed on May 8, 2001, and provisional application No. 60/314,970, filed on Aug. 24, 2001.

(51) Int. Cl.[7] .................................................. A23J 1/00
(52) U.S. Cl. ........................ 530/412; 530/300; 530/350
(58) Field of Search ................................ 530/412, 300, 530/350

(56) References Cited

U.S. PATENT DOCUMENTS

| | | | |
|---|---|---|---|
| 3,112,249 | A | 11/1963 | Toulmin |
| 4,290,774 | A | 9/1981 | Girgis et al. |
| 4,762,792 | A | 8/1988 | Girgis et al. |
| 5,633,349 | A | 5/1997 | Reichl |
| 5,756,678 | A | 5/1998 | Shenoy et al. |

FOREIGN PATENT DOCUMENTS

| | | |
|---|---|---|
| EP | 0 742 018 | 11/1996 |
| EP | 0 937 735 | 8/1999 |

OTHER PUBLICATIONS

Masterton 1977. Chemical Principles, Fourth Edition, pp. 450, 451, 457.*

Appel, TR. et al. "Heat Stability of prion rods and recombinant prion protein in water, lipid and lipid–water mixtures", *Journal of General Virology* (2001) 465–473.

Brown, P. et al. "Newer data on the inactivation of scrapie virus or Creutzfeldt–Jakob disease virus in brain tissue", *Journal of Infectious Disease* (1996) 1145–1148.

Horwich & Weissman "Deadly Conformations: Protein misfolding in prion disease", *Cell* (1997) 499–510.

Simons & Ehehalt "Cholesterols, lipid rafts and disease", *Journal of Clinical Investigation* (2002) 597–603.

Taylor, DM, "Inactivation of BSE–Like Agents", *USAHA Web—2001 USAHA Proceedings: Inactivation of BSE–Like Agents* (2001).

PL107–9 Interagency Working Group Report "Animal disease risk assessment, prevention and control act of 2001: Final report" Jan. 2003.

POST Technical Report "BSE and CJD: Science, Uncertainty and Risk" Apr. 1996.

Prusiner, SB, et al., Proceedings of the National Academy of Science USA, vol. 78, No. 7, Jul. 1981, pp. 4606–4610.

Brown, et al., Transfusion, *The distribution of infectivity in blood components and plasma derivatives in experimental models of TSE transfusion* 1998:38:810–816.

Darbord, J. C., *Biomed & Pharmacother.* 1999; 53 : 34–8.

Dormont, "Agents that cause transmissible subacute spongiform encephalopathies," *Biomed & Pharmacother*, 1999:53–3–8.

Ernst, Darwin R. and Richard E. Race, in "Comparative analysis of scrapie agent inactivation methods" *Journal of Virological Methods*, 41 (1993) 193–202.

Foster et al., Transfusion, Microbiology and Plasma Fractions, Vox Sang, *Studies on the Removal of Abnormal Prion Protein by Processes Used in the Manufacture of Human Plasma Products* 2000; 78: 86–95.

Memorandum from a WHO Meeting, Bulletin of the World Health Organization, 70(2): pp 183–190 (1992).

Taylor, D. M. et al., in "Decontamination studies with the agents of bovine spongiform encephalopathy and scrapie", *Arch. Virol.* (1994) 139: 313–326.

\* cited by examiner

*Primary Examiner*—Karen Cochrane Carlson
(74) *Attorney, Agent, or Firm*—Sherry M. Knowles; Stephanie D. Adams; King & Spalding LLP

(57) ABSTRACT

A process for treatment of a purified lipoprotein material to inactivate prions in a manner that does not substantially adversely affect the biological activity of the lipoprotein is provided that includes treating the lipoprotein prion composition with a solution of base at a pH of between 10 and 13 for a sufficient time to cause inactivation.

41 Claims, No Drawings

PROCESS FOR INACTIVATING PRIONS IN LIPOPROTEINS

The application claims priority to U.S. Ser. Nos. 60/289,637 filed on May 8, 2001, and 60/314,970 filed on Aug. 24, 2001.

FIELD OF THE INVENTION

The invention is a process that reduces, eliminates or inactivates the agent that causes transmissible spongiform encephalopathy (TSE) from lipoproteins in a manner that does not adversely affect the biological activity of the lipoproteins.

BACKGROUND OF THE INVENTION

Water-insoluble lipids like cholesteryl esters, triglycerides and the more polar phospholipids and unesterified cholesterol must travel through the aqueous environment of plasma (Bradely, W. A. and Gotto, A. M.: American Physiological Society, Bethesda, Md., pp 117–137 (1978)). The solubility of these lipids is achieved through physical association with proteins termed apolipoproteins, and the lipid-protein complexes are called lipoproteins (Dolphin, P. J., Can. J. Biochem. Cell. Biol. 63, 850–869 (1985)). Five distinct classes of lipoproteins have been isolated from human plasma: chylomicrons, very low density lipoproteins (VLDL), low density lipoproteins (LDL), high density lipoproteins (HDL) and lipoprotein (a) (Lp(a)) (Alaupovic, P. (1980) In Handbook of Electrophoresis. Vol. 1, pp. 27–46; Havel, R. J., Eder, H. A.; Bragdon, J. H., *J. Clin. Invest.* 34, 1343 (1955)). Dietary triglycerides and cholesterol are assembled by enterocytes (intestinal cells) into a chylomicron particle, which enters circulation through the lymphatic system (Brown, M. S. and Goldstein, J. L Sci. American (1984) 251, 58–66). Chylomicrons provide fatty acids to peripheral cells and cholesterol to liver. The liver in turn repackages cholesterol together with triglycerides into another lipoprotein called VLDL.

The function of VLDL is similar to chylomicrons, i.e. supply of free fatty acids to the muscle and adipose tissues and cholesterol to peripheral cells (Brown, M. S. and Goldstein, J. L Sci. American (1984) 251, 58–66). In the circulatory system, triglycerides in the VLDL particle are hydrolyzed by an enzyme called lipoprotein lipase (LPL) and additional processing by hepatic lipase finally converts it to LDL (Dolphin, P. J.: Can. J. Biochem. Cell. Biol. (1985) 63, 850–869). Thus, the liver produces VLDL, the precursor of LDL. Because VLDL is a precursor to LDL, decreases in VLDL production translate into lowered LDL levels. High levels of circulating LDL have been positively correlated with the development of coronary disease. While LDL cholesterol is clearly an independent positive risk factor, HDL cholesterol is considered to be a negative risk factor (Tribble, D. L.; Krauss, R. M. Advances in Internal Medicine (1993) 38:1–29).

HDL promotes reverse cholesterol transport, a process by which excess cholesterol is extracted from peripheral cells by HDL and delivered to the liver for its elimination. Reverse cholesterol transport, therefore, reduces cholesterol accumulation in the artery wall (Reichl, D and Miller, N. E., *Arteriosclerosis* 9, 785 (1989)). Because there is no cholesterol accumulation in extrahepatic organs, cholesterol must be transported to the liver by HDL for ultimate excretion into bile, either as free cholesterol, or as bile acids that are formed from cholesterol (Kwiterovich, P. O., *Amer. J. Cardiol.* 82, 13Q, (1998)). HDL can acquire part of its anti-atherogenic character by promoting the reverse transport of cholesterol.

In humans, low HDL cholesterol levels can relate to defects in synthesis or catabolism of Apo-Al, with catabolic defects being more common (Brinton, E. A., et al., *Ateriosclerosis Thromb.* 14, 707 (1994)); Fridge, N., et al., *Metabolism* 29, 643 (1980)). Low HDL is often associated with hypertriglyceridemia, obesity, and insulin resistance (Brinton, E. A., et al., *Aterioscle*rosis *Thromb.* 14, 707 (1994)). HDL from hypertriglyceridemic subjects characterized by low HDL levels have small HDL particles which are susceptible to renal filtration and degradation. The liver is the principal organ of HDL apolipoprotein degradation (Horowitz, B. S., et al., *J Clin. Invest.* 91, 1743 (1993)).

HDL has other important characteristics that can contribute to its anti-atherogenic properties. Recent evidence suggests that HDL can have antioxidant and antithrombotic properties (Tribble, D., et al., *J. Lipid Res.* 36, 2580 (1995); Mackness, M. I., et al., *Biochem. J.* 294, 829 (1993); Zeither, A. M., et al., *Circulation* 89, 2525 (1994)). HDL can also affect the production of some cell adhesion molecules such as vascular cell adhesion molecule-1 (VCAM-1) and intercellular adhesion molecule-1 (ICAM-1), (Cockerill, G. W., et al., *Arterioscler. Thromb.,* 15, 1987 (1995)). These properties of HDL also provide protection against coronary artery disease.

Cholesterol and cholesterol-containing lipoproteins obtained from mammalian serum are also useful to promote the growth of various organisms. J. Bacteriol., Vol. 135, pp. 818–827 (1978) describes the use of a cholesterol-containing bovine serum fraction in the growth of Mycoplasma pneumoniae and Mycoplasma arthritidis. J. Gen. Microbiology, Vol. 116, pp. 539–543 (1980) describes the use of USP cholesterol in the growth of Treponema hyodysenteriae.

U.S. Pat. No. 4,290,774 describes the production of a specific cholesterol-rich fraction from mammalian plasma or serum by a process that involves the step of treatment with an alkaline carbonate and an alkaline earth salt. Zeit. Klin. Chem. 6(3), pp. 186–190 (1968) describes the removal of certain lipoproteins from human serum by use of colloidal silicic acid.

U.S. Pat. No. 4,762,792 discloses a process for isolating a cholesterol-rich fraction from mammalian blood plasma or serum using a silica adsorbant followed by several alkaline steps.

Transmissible Spongiform Encephalopathy

The transmissible degenerative encephalopathies, also known as spongiform encephalopathies or transmissible spongiform encephalopathies (TSE), constitute a distinct group of fatal neurological diseases of mammals. In 1994, Prusiner described the "remarkable discoveries in the past three decades (which have) led to the molecular and genetic characterization of the transmissible pathogen causing scrapie in animals and several illnesses in humans: Kura, Creutzfeldt Jacob Disease (CJD), Gerstmann-Straussler-Scheinker disease, and Fatal Familial Insomnia. To distinguish this infectious pathogen from viruses and viroids, the term PRION was introduced to emphasize its proteinaceous and infectious nature." Prusiner, "Biology and Genetics of Prion Diseases," *Annu. Rev. Microbiol.* 48:655–686 (1994). A prion is composed solely of one host-encoded protein (referred to as the "PrP") that resists most inactivation procedures such as heat, radiation and/or proteases. The latter characteristic has led to the term "protease-resistant isoform" of the prion protein. Amino acid sequences of PrP obtained from normal and infected brains are identical, and these two proteins differ only in their biochemical and biophysical behavior. In particular, PrP from TSE individuals resists proteinase K digestion, while PrP-c found in normal individuals is degraded by proteinase K. PrP-res is not associated with an increase in mRNA, instead the accumulation is post-translational. Infected animals accumulate their own PrP-res, not that used for, or which created, the infection (Dormont, *Agents that cause transmissible subacute spongiform encephalopathies*, Biomed & Pharmacother 1999:53:3–8).

Prions resist almost all of the general procedures used to inactivate conventional viruses. Dormont, id.

Mad cow disease, or bovine spongiform encephalopathy (BSE), is the most well known TSE. All of the transmissible spongiform encephalopathies are progressive degenerative disorders that affect the central nervous system of animals and humans. These neurologic diseases take part of their name from the spongiform or "sponge-like" degeneration of brain tissue that they cause. These diseases share many clinical and pathological features, and some scientific evidence now suggests that they develop through common or closely related mechanisms. This degeneration is most common in the cerebral cortex, the basal ganglia and the thalamus. Among other unique features, all of these diseases are associated with the accumulation of an abnormal form of the prion protein in nerve cells that eventually leads to the death of the host.

These diseases can be transmitted from one host to another much like an infection; unlike more typical forms of infectious diseases; however, the transmissible spongiform encephalopathies have incubation periods that are measured in intervals of months to many years. While prion diseases can all be transmitted from one host to another, it remains unknown whether a virus-like infectious agent or the abnormal prion protein itself (prion) causes the conversion of normal to abnormal protein.

In some cases, transmissible spongiform encephalopathies develop through genetic mutations and therefore occur as familial or hereditary disorders. Regardless of the cause (sporadic, infectious or familial), once the disease has manifested itself, it typically progresses over a period of months and inevitably leads to the death of the affected host. Questions about how these diseases are transmitted and whether they can cross species barriers remain only partially answered. Evidence does exist that BSE can be passed to humans as the so-called New-variant Creutzfeldt-Jakob Disease. Such issues command much of the current public attention about these otherwise rare neurologic disorders.

Examples of animal prion diseases include scrapie, which affects sheep and goats and takes its name from the tendency of affected animals to scrape against objects to relieve itching; transmissible mink encephalopathy, chronic wasting disease, which affects mule deer and elk; bovine spongiform encephalopathy; spongiform encephalopathy of exotic ruminants; and feline spongiform encephalopathy. Examples of currently identified human prion diseases include Kuru, Creutzfeldt-Jakob Disease, whether sporadic, familial, or iatrogenic, Fatal Familial Insomnia, Gerstmann-Straussler-Scheinker Syndrome, and New-variant Creutzfeldt-Jakob Disease.

The evidence of transmissibility of prion diseases between species has created fear. This is best evidenced by the destruction of cattle and bans on the importation of beef and cattle from Britain following an increased number of cases of mad cow disease. More information regarding aspects of prion diseases can be found at: www.jhu-prion.org and also at other internet sites.

A substantial amount of research has been carried out to determine how to inactivate prions from a range of materials. Researchers in general have found that it is a difficult task to identify successful conditions to achieve inactivation, and due to the severe conditions required, there has been little ability to correlate successful conditions in one composition to another. The most important reason for the inability to have a reasonable expectation of success in treating a previously untreated solution is that the conditions to treat the prion must be harsh (typically more extreme than those that are known to kill viruses), yet the conditions must be mild enough not to adversely affect the biological activity of the other components of the composition, if that material is to be used subsequently for a biological purpose, and is not merely being sterilized. This represents a difficult and sensitive balance.

For example, U.S. Pat. No. 5,756,678 to Shenoy, issued on May 26, 1998, describes that the inventors had discovered that it is possible to treat solutions of connective tissue material for the inactivation of prions in a manner that connective tissue molecules are not adversely affected by the inactivation treatment. The inventors found that treatment of the collagen with 0.1 to 0.35M NaOH inactivated the prions, but that the collagen was adversely affected unless they took the extra step of solubilizing the collagen prior to treatment. The inventors wrote:

> From a prion deactivation perspective, it is preferable to treat a solution of collagen with sodium hydroxide rather than to treat precipitated fibers in a dispersion. The soluble collagen molecule and any beginning fibrils which are in solution are dissociated to permit maximum availability of any infectious agents which can reside in or be trapped with fiber structures. The collagen triple helix is too tightly wound (1.5 nm diameter) for viruses and prions (to the extent that they are known) to reside within the collagen molecule. Therefore, such virus or prion would be present either in the solution or absorbed onto the surface of a collagen molecule. In the soluble environment, where collagen fibers are dissociated into collagen molecules, there is no mass transfer barrier which requires the sodium hydroxide to diffuse through solids (assembled fibers) to reach the infectious agents on the surface of collagen molecules.

'678 patent, column 16, lines 20–35.

J. C. Darbord (Biomed & Pharmacother. 1999; 53: 34–8) described the ability of several procedures to sterilize medical laboratory materials that have come into contact with prion-infected tissue. Sterilizing conditions recommended by World Health Organization are a) incineration or quarantine; b) soaking in 1 N sodium hydroxide (1 h, 20° C.); c) soaking in 17.5% bleach (1 h, 20° C.) and d) steam sterilization in autoclave (134° C.–138° C., 18 min).

The first study of the distribution of the TSE prion during plasma fractionation found partitioning to occur predominantly into the initial precipitates obtained during the fractionation of murine plasma from animals infected with a human TSE, and from plasma prepared from human blood to which hamster-adapted scrapie 263K had been added. However, the distribution of TSE was not fully determined (Brown, et al., Transfusion, *The distribution of infectivity in blood components and plasma derivatives in experimental models of TSE transfusion* 1998:38:810–816).

Foster et al. (Transfusion, Microbiology and Plasma Fractions, Vox Sang, *Studies on the Removal of Abnormal Prion Protein by Processes Used in the Manufacture of Human Plasma Products* 2000; 78: 86–95), concluded that plasma ethanol fractionation processes used in the manufacture of albumin, immunoglobulin, factor-VIII concentrate, factor-IX concentrates, fibrinogen and thrombin all contain steps which can be capable of removing causative agents of human TSEs but that further studies are required.

Recommendations for Minimizing the Risk of Infection by Agents Causing Zoonoses and Other Animal Infections in the Manufacture of Medicinal Products, Federal Journal of Official Publications (BAnz., Germany), No. 164, p.6120 (1991), describes the sterilization of medical materials with a solution of 1N (1M) NaOH for one hour at 20° C. for the purpose of inactivation of infectious agents. This treatment was recommended particularly for application to bovine spongiform encephalopathy (BSE) and materials of bovine origin.

Public Health Issues Related to Animal and Human Spongiform Encephalopathies: Memorandum from a WHO Meeting, Bulletin of the World Health Organization, 70(2): pp 183–190 (1992) recommended that medicinal products derived from bovine tissues be treated with NaOH, preferably 1M, for 1 hour at 20° C. during the manufacturing process for removal or reduction of BSE infectivity.

Darwin R. Ernst and Richard E. Race, in "Comparative analysis of scrapie agent inactivation methods" Journal of Virological Methods, 41 (1993) 193–202, describe inactivation treatments for scrapie-infected hamster brain homogenate. Inactivation treatments utilizing autoclaving for various lengths of time either alone or in combination with different concentrations of sodium hydroxide, or an aqueous acid phenolic derivative, was disclosed. Although this paper indicates that treatment of suspensions of hamster brain using either 0.1N or 1.0N NaOH alone was carried out, no data are presented. D. M. Taylor et al., in "Decontamination studies with the agents of bovine spongiform encephalopathy and scrapie", Arch. Virol. (1994) 139: 313–326, describe the use of sodium hydroxide to treat macerates of bovine brain infected with bovine spongiform encephalopathy (BSE) agent; rodent brain infected with the 263K strain of scrapie agent; and, rodent brain infected with the ME7 strain of scrapie agent. The macerates were exposed for up to 120 minutes to 1.0M or 2.0M sodium hydroxide, but "no procedure produced complete inactivation of all agents tested. Taylor et al. explained that the study was carried out due to inconsistencies in the data from various laboratories. They found that the data from the NaOH inactivation experiments demonstrated that none of the combinations of time (30 minutes up to 120 minutes) and molarity (1M and 2M) produced consistent inactivation of BSE and scrapie agents. Further, there was the unexplained finding in the NaOH experiments that with the 263K strain, with BSE, and possibly with ME7, two hours of exposure were less effective than exposure periods for 30 or 60 minutes.

In 1994 it was reported that homogenates of BSE-infected bovine brain exposed to less than or up to 120 minutes to solutions of sodium hypoclorite resulted in sterilization of the material, but that dichloroisocyanurate did not produce complete deactivation, nor did 1M or 2M sodium hydroxide treatment for up to 120 minutes. Taylor, et al., *Decontamination studies with the agents of bovine spongiform encephalopathy and scrapie Arch Virol* (1994) Archives of Virology 139:313–326.

In reviewing the literature on attempts to inactivate prions, it is clear that the intention of much of the work has been to sterilize material, i.e., to destroy the prion without regard to the effect on the infected material, as opposed to finding conditions that destroy the prion while not adversely affecting the base infected material. This is seen from the severity of conditions used, i.e., autoclaving, treatment with hypochlorite (which oxidizes biological materials) and strong base (which can denature or degrade biological material).

Given the important biological uses of lipoproteins isolated from biological sources, and the risk of infection with prions, it is a goal of the present work to provide a process to reduce or eliminate prions from lipoprotein containing material.

It is an object of the present invention to provide a method to inactivate prions from a lipoprotein in a manner that does not substantially adversely affect the biological activity of the lipoprotein.

It is another object of the invention to provide a method to inactivate prions from an optionally-cholesterol carrying lipoprotein in a manner that does not substantially adversely affect the biological activity of the lipoprotein, wherein the lipoprotein is mammalian high density lipoprotein or low density lipoprotein.

It is still another object of the invention to provide a method to inactivate prions from an optionally-cholesterol carrying lipoprotein in a manner that does not substantially adversely affect the biological activity of the lipoprotein, wherein the lipoprotein is bovine lipoprotein.

It is another object of the invention to provide a method to inactivate prions from an optionally-cholesterol carrying lipoprotein composition that partially or completely sterilizes the composition.

It is another object of the invention to provide a method to inactivate prions from an optionally-cholesterol carrying lipoprotein composition that partially or completely sterilizes the composition, wherein the lipoprotein is mammalian high density lipoprotein or low density lipoprotein.

It is another object of the invention to provide a method to inactivate prions from an optionally-cholesterol carrying lipoprotein composition that partially or completely sterilizes the composition, wherein the lipoprotein is bovine high density lipoprotein or low density lipoprotein.

SUMMARY OF THE INVENTION

A process for treatment of a purified lipoprotein material to inactivate prions in a manner that does not substantially adversely affect the biological activity of the lipoprotein is provided that includes treating the lipoprotein prion composition with a solution of base at a pH of between 10 and 13 for a sufficient time to cause inactivation.

The term purified lipoprotein material refers to material (i) that can include any lipophilic compound that is typically carried through the plasma by apolipoproteins, including but not limited to cholesteryl esters, unesterified cholesterol, triglycerides, fatty acids and/or phospholipids; and (ii) that is in a higher state of purity than that found naturally in biological materials such as tissue or brain homogenate. In preferred embodiments, the purified lipoprotein material constitutes up to 60, 70, 80 or 90 percent or higher by weight of the material being treated. In one embodiment, the lipoprotein and cholesterol are in substantially pure form, i.e., the material being treated consists essentially of lipoprotein material.

In an alternative embodiment, purified lipoprotein material is treated with a base at a pH of above 8 or 9 to 13 inactivate prion for a period of time from initial contact up to 8 to 10 hours or more, preferably at approximately room temperature.

It was surprising to find that this treatment inactivates prions in the lipoprotein while not destroying or unduly affecting the sensitive biological material. It was not known prior to this work whether the lipoprotein would shield the prion from inactivation, or whether any condition could be found that inactivated the prion without also harming the lipoprotein. In one embodiment, the lipoprotein is treated as a somewhat dilute solution, to allow the base to easily penetrate the lipoprotein, enveloped by the more water soluble apolipoprotein.

Any suitable alkaline agent can be utilized to adjust the pH. According to one example, NaOH in a 1N solution was added to the lipoproteins to achieve an elevated pH of between 10 to about 13. The exposure to the elevated pH can include any exposure from the briefest possible exposure up to 8–10 hours. The lipoproteins can be exposed to an alkaline agent and the agent immediately neutralized. In such case, the pH is not maintained at the elevated pH, but rather adjusted to the elevated value and then immediately readjusted for minimal impact on the biological material. It appears that even such a brief exposure can help to reduce the TSE causing agent. Even though the pH exposure can be contact only, the exposure is typically at least about 2, 3, 4, 5, 6, 7, 8, 9, 10, 11, or 12 hours. More typically, the pH is maintained at about 10 to about 13 for about 2 hours to about 8 hours. According to one embodiment, the solution is maintained at a pH of about 12 for about 8 hours. Longer periods of time can be utilized for the elevated pH exposure if deemed desirable and/or necessary. Those of ordinary skill in the art, once aware of the disclosure contained herein can determine acceptable pH levels and time periods without undue experimentation.

In another embodiment, any base can be used that does not denature or otherwise adversely affect the lipoprotein. For example, potassium hydroxide or other source of basic hydroxide ion that does not denature or otherwise adversely affect the lipoprotein can be used. Alternatively, the base can be an ammonium ion or amine, including mono or di(alkyl or alkanol)amine, or a carbonate or bicarbonate or mixture thereof, such as potassium or sodium carbonate or bicarbonate or a combination thereof. If the lipoprotein is to be used for a biological purpose, it is important that a base be used that will not leave a toxic residue.

Time and pH appear to be related, in that the higher the pH used, the shorter the amount of time that the infected material can or perhaps should be treated, to minimize the adverse affect on the lipoprotein material. The elevated pH exposure step can be carried out at any desired temperature, optimally between about 16° C. and about 24° C. According to one particular embodiment, the elevated pH exposure step was carried out at a temperature of room temperature, or about 20° C. Temperature and time are related as are pH and time. For example, a higher temperature may be utilized for a shorter period of time, again to prevent an adverse affect on the treated lipoprotein material.

The lipoproteins treated by this process maintain their usefulness, for example, as a growth enhancement media supplement. Known processes do not disclose or suggest a process for producing a growth enhancement media supplement, wherein the process reduces, eliminates, or inactivates transmissible spongiform encephalopathy agent that can be present in portions of the raw materials used in the process to result in a final product that has little or no TSE agent present.

A typical but not necessary range of lipoprotein concentration in the treatment solution is between 10 and 3,500, and more particularly between 10 and 1,500 mg/dL. One particularly preferred range is between 50 and 500 mg/dL. After treatment with the base for a sufficient time to allow a desired degree of prion inactivation, the pH can be adjusted to neutral or another desired pH, using a pH-adjusting agent that does not adversely affect the biologic material.

In one embodiment a process for inactivating prions from a lipoprotein solution is provided, wherein the solution (other than contaminating prion) consists substantially or essentially of lipoprotein (optionally along with any lipophilic material carried by apolipoproteins through the plasma such as fatty acids, triglycerides, phospholipids or cholesterol), solvent, along with an insubstantial amount of other biological materials such as albumin. In one embodiment, the lipoprotein is (other than contaminating prion) substantially pure lipoprotein that may contain cholesterol. In a broader embodiment, the protein other than lipoprotein is present in less than 5, 4, 3, 2, 1, or 0.5% by weight.

In another embodiment, the solution contains at least approximately 0.1 to 8% by weight of optionally cholesterol bearing lipoprotein, and in particular up to approximately 0.1, 0.5, 1, 2, 4, 6, or 8% by weight of optionally cholesterol bearing lipoprotein.

In another embodiment the lipoprotein material consists substantially or essentially of HDL or LDL or combination thereof optionally in association with cholesterol, in an appropriate solvent. In a non limiting embodiment solvent can be, for example, water, saline, buffer, or any other aqueous solvent that does not adversely affect the biological properties of the material. Solutes that do not adversely or materially affect the biological properties of the material or the deactivation process can be included in the solution.

In a further embodiment, the lipoprotein material after prion deactivation is effective for use as a component of cell growth media.

In another embodiment, the treated lipoprotein is used for a purpose other than as nutrient in cell growth media, for example, as a source of lipoprotein for a host animal or organism in need thereof, for desired cholesterol transport, or for other biological purposes, including those associated with the presence of other lipophilic components such as fatty acids or phospholipids.

In another embodiment, prions are removed from a lipoprotein solution by contacting the solution with an adsorbant, preferably silica, which binds more tightly to the lipoprotein than to the prion. For example, the lipoprotein can be mixed with silica at a pH that does not cause the removal of the lipoprotein from the silica, typically between 6 and 8, and then the silica/lipoprotein particulate is separated from the prion-containing liquid by filtration. The lipoprotein is then removed from the silica using any appropriate method, for example, at an elevated pH. According to one embodiment, the recovery is carried out at a pH of about 10.5. According to another embodiment, the recovery is carried out by passing a high pH buffered solution through the lipoprotein-adsorbent complex until the lipoprotein is substantially removed from the adsorbent. After recovering the purified lipoproteins, the adsorbent can be discarded.

Still other objects and advantages of the present invention will become readily apparent by those skilled in the art from a review of the following detailed description. The detailed description describes preferred embodiments of the present invention, by way of illustration. As will be realized, the present invention is capable of other and different embodiments and its several details are capable of modifications in various obvious respects, without departing from the invention. Accordingly, the description is illustrative in nature and not meant to restrict the scope of the invention.

DETAILED DESCRIPTION OF THE INVENTION

It has been discovered that prions can be inactivated from lipoprotein material in a manner that does not substantially adversely affect the biological activity of the lipoprotein, by treating the lipoprotein with a solution of sodium hydroxide or other base to a pH of between 10 (or even pH 8 or 9) and 13 for a period of time from contact to 8 to 10 hours, preferably at approximately room temperature. It was surprising to find that this treatment inactivates prions in the lipoprotein material while not destroying or unduly affecting the sensitive biological material. It was not known prior to this work whether the lipoprotein material would shield the prion from inactivation, or whether any condition could be found that inactivated the prion without also harming the lipoprotein. In one embodiment, the lipoprotein material is treated as a somewhat dilute solution, to allow the base to easily penetrate the lipoprotein, enveloped by the more water soluble apolipoprotein. An example of the range of lipoprotein concentration is between 10 and 3,500 mg/dL, and one particularly preferred range is between 50 and 200 mg/dL. After treatment with the base for a sufficient time to allow a desired degree of prion inactivation, the pH can be adjusted to neutral or another desired pH, using a pH-adjusting agent that does not adversely affect the biologic material.

Any base can be used that does not denature or otherwise adversely affect the lipoprotein. For example, sodium hydroxide or potassium hydroxide or other source of basic hydroxide ion that does not denature or otherwise adversely affect the lipoprotein can be used. Alternatively, the base can be an ammonium ion or amine, including mono or di(alkyl or alkanol)amine, or a carbonate or bicarbonate or mixture thereof, such as potassium or sodium carbonate or bicarbonate or a combination thereof. If the lipoprotein is to be used for a biological purpose, it is important that a base be used that will not leave a toxic residue.

The lipoproteins that are treated according to this invention, for example, can be that taken from any TSE infected animal blood plasma or serum fraction, and in particular, from a mammal, including that from bovine, horse, sheep, pig or human plasma or serum or fraction thereof, such as fibrinogen-poor plasma, Cohn Fraction I supernatant, ammonium sulfate supernatant rich in lipoprotein and other fractions. Typical source materials are bovine serum and bovine plasma.

In one embodiment a process for inactivating prions from a lipoprotein solution is provided, wherein the solution consists substantially or essentially of lipoprotein material and solvent, along with an insubstantial amount of other biological materials, for example, albumin.

In another embodiment, the solution contains at least approximately 0.1 to 8% by weight of lipoprotein material, and in particular up to approximately 0.1, 0.5, 1, 2, 4, 6, or 8% by weight of lipoprotein material.

In another embodiment the solution consists substantially or essentially of HDL or LDL or combination thereof optionally in association with cholesterol, in an appropriate solvent. In a non-limiting embodiment solvent can be, for example, water, saline, buffer or any other aqueous based that does not adversely affect the biological properties of the material. Solutes that do not adversely affect the biological properties of the material or the deactivation process can be included in a solution.

In a further embodiment, the lipoprotein material after prion inactivation is used as a component of cell growth media.

In another embodiment, prions are removed from a lipoprotein material solution by contacting the solution with an adsorbant, preferably silica, which binds more tightly to the lipoprotein than to the prion. For example, the lipoprotein can be mixed with silica at a pH that does not cause the removal of the lipoprotein from the silica, typically between 6 and 8, and then the silica/lipoprotein particulate is separated from the prion-containing liquid by filtration. The lipoprotein is then removed from the silica using any appropriate method, for example, at an elevated pH. According to one embodiment, the recovery is carried out at a pH of about 10–11. According to another embodiment, the recovery is carried out by passing a high pH buffered solution through the lipoprotein-adsorbent complex until the lipoprotein is substantially removed from the adsorbent. After recovering the purified lipoproteins, the adsorbent can be discarded.

The following provides illustrations of the process according to the present invention. The general discussion is followed by examples of two specific embodiments. The effectiveness of the present invention in eliminating transmissible spongiform encephalopathy agents is further discussed below.

EXAMPLES

Example 1
Method to Obtain Cholesterol-Rich Fraction from Bovine Serum with Base Deactivation Starting material for a process according to the present invention can be maintained at a temperature of about 0° C. to about 50° C. Typically, the temperature is maintained at about 2° C. to about 15° C. A process according to the present invention can begin by subjecting the starting material to filtration. The filtration can be carried out utilizing one or more filtration steps. According to one embodiment, two filtration steps are sequentially utilized with filters having a nominal porosity of about $5\mu$ and about $1\ \mu$u. Any suitable filter in this range can be utilized.

If the starting material is serum, it is preferred to add a soluble salt, such as sodium citrate, to an ionic strength of about 0.25 to about 1.0. Other suitable salts include sodium chloride, sodium phosphate, potassium phosphate, ammonium sulfate and sodium sulfate. The addition of a soluble salt to the above concentration will increase the amount of cholesterol-rich fraction adsorbed in the subsequent silica adsorption step. Bovine or human plasma, for example, is normally collected by a method, which includes addition of citrate as an anti-coagulant. This salt concentration is usually sufficient for the adsorption step and no additional salt is needed. After adding the soluble salt, the solution can be mixed. Typically, the solution is mixed for about 30 minutes.

After addition of sodium citrate, other materials that can facilitate processing can be added to the starting material and any added soluble salt(s). According to one example, polyethyleneglycol (PEG) can be added to the filtered starting material. PEG having a range of molecular weights can be utilized. According to one example, PEG having an average molecular weight of about 3350 is utilized. However, PEG having greater or lesser molecular weights can also be utilized. Along these lines, PEG having an average molecular weight of about 6000 could be utilized. One of ordinary skill in the art, once aware of the disclosure contained herein would be able to determine the molecular weight of PEG to utilize with out undue experimentation. The PEG can be added in an amount of about 10 grams to about 15.6 grams for each liter of filtered starting material and sodium citrate, if utilized. After addition of the PEG the solution can be mixed. Typically, the solution is mixed for about 30 minutes, although shorter or longer mixing times can be utilized. While the addition of PEG can facilitate the purification process, it is not necessary.

After addition of the PEG, if utilized, the pH can be adjusted to a slightly acidic value. Along these lines, the pH can be adjusted to a value of about 5 to about 8. Typically, the pH is adjusted to a value of about 5.8 to about 6.2

After filtration, the lipoproteins in the filtered raw material are adsorbed onto an adsorbent. Any suitable adsorbent can be utilized. One example is silica-containing adsorbents. A silica adsorbent useful in this invention does not have a critical composition. Appropriate silica materials are the microfine silica available under the trademark Cabosil from Cabot Corporation and AEROSIL and SIPERNAT, such as the powdered silica SIPERNAT 50, manufactured by DeGussa and available from Cary Co. The silica is added to the liquid plasma or serum in an amount of about 1 to about 50 g/L, typically about 10 to about 20 g/L. The silica suspension in the liquid plasma or serum is then mixed for about 3 to about 4 hours.

The adsorption can be carried out at a slightly acidic pH. Along these lines, the adsorption can be carried out at a pH of about 5 to about 8. Typically, the adsorption is carried out at a pH of about 5.8 to about 6.2. According to one example, the adsorption is carried out at a pH of about 6. Additionally, the adsorption can be carried out at a temperature of about 15° C. to about 30° C. for about 2 hours to about 24 hours. After adding the adsorbent(s), the solution can be mixed. According to one embodiment, the solution is mixed for about 30 to about 6 hours.

After adsorption, the lipoprotein-adsorbent complex can be isolated and remaining portion of the raw material discarded. The isolation can be carried out as a simple phase separation utilizing a filter press.

Subsequent to isolating the lipoprotein-adsorbent complex, occluded serum proteins can be removed from the lipoprotein-adsorbent complex. The removal can be carried out utilizing a high salt buffer wash. According to one example, this can be accomplished by washing the lipoprotein-adsorbent complex with an aqueous salt solution containing about 0.15 M sodium chloride. Other useful salts can include sodium acetate and/or sodium phosphate. The pH of the solution can also vary. Typically, the pH of the wash solution is about 6.9 to about 7.1. Similarly, the temperature that the wash is carried out at can vary. Typically, the temperature is about 2° C. to about 30° C. The salt solution is used in an amount about 120 liters for about each kilogram of the lipoprotein-adsorbent complex. Typically, the total volume of wash solution utilized could be about 12,000 liters to about 24,000 liters. According to one embodiment, two wash steps are carried out, each utilizing about 12,000 liters of wash solution. According to another embodiment, two wash steps could be carried out, each utilizing about 6,000 liters of solution. However, the volume could be more or less. The washing can be accomplished as a batch process or in a continuous washing process. According to one embodiment, the washing procedure is carried out at least two times as a batch process to remove occluded proteins. According to one particular embodiment, a first wash is carried out utilizing about 12,000 liters of a solution that contains about 8.3 to about 9.2 grams sodium chloride per liter and about 2.1 to about 2.9 grams sodium phosphate per liter at a pH of about 6.9 to about 7.1 and at a temperature of about 2° C. to about 30° C. This embodiment also includes carrying out a second washing step with about 12,000 liters of a solution that includes about 2.1 to about 2.9 grams sodium phosphate per liter at a pH of about 6.9 to about 7.1 at a temperature of about 2° C. to about 30° C. In embodiments that utilize a filter press to carry out the washing, the washing, whether a batch or continuous process, continues until reaching a target absorbance for the wash collection. According to one embodiment, the absorbance is less than about 0.1 at 280 nm. After washing the isolated the lipoprotein-adsorbent complex, the material utilized to remove the occluded proteins can be discarded.

The purified lipoproteins can then be recovered from the adsorbent. The recovery can be carried out at an elevated pH. According to one embodiment, the recovery is carried out at a pH of about 10.5. According to another embodiment, the recovery is carried out by passing a high pH buffered solution through the lipoprotein-adsorbent complex until cholesterol is substantially removed from the adsorbent. After recovering the purified lipoproteins, the adsorbent is discarded.

A solution containing the recovered lipoproteins can then be filtered. The filtration can be carried out utilizing one or more filtration steps. According to one embodiment, two filtration steps are utilized. A first filtration step utilizes filters having a nominal porosity of about $1\mu$. A second filtration step utilizes membrane filters having a porosity of about $0.45\mu$. In this and any of the filtration steps described herein, other filters can be utilized having different porosities as long as the porosity results in filtering particles of the desired size. Those of ordinary skill in the art would be able to determine suitable filter porosities without undue experimentation.

After filtration, the recovered lipoproteins are exposed to an elevated pH. Exposing the recovered lipoproteins to the elevated pH appears to be significant in eliminating transmissible spongiform encephalopathy agent present in the recovered lipoproteins. Any suitable alkaline agent can be utilized to adjust the pH. According to one example, NaOH in a 1N solution was added to the recovered lipoproteins to achieve an elevated pH of between 10 to about 13. The exposure to the elevated pH can include any exposure from the briefest possible exposure up to many hours. Along these lines, the recovered lipoproteins can be exposed to an alkaline agent and the agent immediately neutralized. In such as case, the pH is not maintained at the elevated pH, but rather adjusted to the elevated value and then readjusted. The exposure in such a case can be as brief as practically possible. It appears, as discussed below, that even such a brief exposure can help to reduce TSE agent. Even though the pH exposure can be fleeting, the exposure is typically at least about 2, 3, 4, 5, 6, 7, 8, 9, 10, 11, or 12 hours. Typically, the pH is maintained at an elevated level for about 2 hours to about 12 hours. More typically, the pH is maintained at about 11 to about 13 for about 2 hours to about 8 hours. According to one embodiment, the solution is maintained at about pH of about 12 for about 8 hours. Longer periods of time can be utilized for the elevated pH exposure if deemed desirable and/or necessary. Those of ordinary skill in the art, once aware of the disclosure contained herein could determine acceptable pH levels and time periods without undue experimentation.

Time and pH appear to be related in that a lower pH can be utilized if the time at the lower pH is longer as compared to higher pH. For example, a pH of about 10.5 can be utilized for a time longer than about 8 hours. A solution maintained at a high pH can be maintained at the lower pH for a comparatively shorter period of time.

The elevated pH exposure step can be carried out at a temperature of about 18° C. to about 22° C. According to one particular embodiment, the elevated pH exposure step was carried out at a temperature of about 20° C. Temperature and time can also be related as pH and time. For example, a higher temperature can be utilized for a shorter period of time.

After the elevated pH exposure step, the recovered lipoproteins can be subjected to additional steps to isolate them. The maintenance steps can include concentration/diafiltration by ultrafiltration. In this portion of the process, the concentrated cholesterol-rich solution can be dialyzed against an alkaline and/or a pH neutral material to further remove adsorbent that includes silica. Examples of materials that could be utilized in the dialysis include sodium carbonate and water. In order to improve the effectiveness of this dialysis step, it is desirable for the cholesterol-rich solution to be at a pH of about 7 to about 13, typically at a pH of about 8. The pH can be adjusted to this value by alkaline or acidic addition. This can take place just prior to the dialysis step, but typically, for operating convenience, the pH is adjusted to this value before the cholesterol-rich solution is subjected to an ultrafiltration concentration step.

In the dialysis step, 8–12 volumes of deionized water can be utilized to remove the sodium carbonate. The resulting solution can then be concentrated by ultrafiltration prior to deionizing.

The concentration/defiltration by ultrafiltration can be carried out until the solution including the recovered lipoproteins is concentrated by about 15 percent to about 50 percent. Typically, the solution is concentrated by about 20 percent to about 25 percent.

The elevated pH exposure can be carried out at least partially during the concentration/diafiltration by ultrafiltration.

Next, the concentrated solution is filtered. The filtration can be carried out utilizing one or more filtration steps. The filters utilized to carry out the filtration can have the capability to remove particles in the range of about 0.1 $\mu$ to about 1.0$\mu$. According to one embodiment, the solution is filtered sequentially through filters having porosities of about 0.65 $\mu$ and about 0.2$\mu$.

Subsequent to filtration, the solution is subjected to a heat treatment. The heat treatment includes exposing the solution to elevated temperatures. The heat treatment can help to eliminate, reduce and/or inactivate viruses or prions that can be present in the solution.

The heat treatment typically includes exposing the solution to a temperature of at least about 60° C. for a period of time of about at least about 10 hours. Typically, the solution is exposed to a temperature of about 60° C. to about 80° C. for a period of time of about 10 hours to about 14 hours. The solution can be exposed to about the same elevated temperature continuously. Alternatively, the solution can be exposed to different temperatures during the heat treatment. According to one embodiment, the heat treatment is carried out in three stages including a first stage at a temperature of about 80° C. for a time period of about 1 hour, a second stage at a temperature of about 65° C. for a time period of about 3 hours, and a third stage at a temperature of about 60° C. for a time period of about 10 hours. Any suitable time and temperature can be utilized to result in the desired effects on the solution. According to one embodiment, the time and temperature utilized in the heat treatment are sufficient to eliminate, reduce and/or inactivate viruses, according to generally accepted techniques for virus elimination, reduction and/or inactivation.

After exposure to the heat treatment, the solution is subjected to filtration. The filtration can be carried out utilizing one or more filtration steps. The filters utilized to carry out the filtration can have the capability to remove particles in the range of about 0.1 $\mu$ to about 1.0$\mu$. According to one embodiment, four filtration steps are utilized to sequentially filter the solution with membrane filters of about 0.65 $\mu$ about 0.45$\mu$, about 0.2$\mu$, and about 0.1$\mu$.

Next, final cholesterol and pH adjustments can be made. While it is not necessary in the process for production of the cholesterol-rich fraction, it is convenient that the product have a pH adjusted to about 7.0 to about 8.4 so that it is generally compatible with media employed for cell culture.

After adjustments to bring the cholesterol and pH to desired levels, the solution can be subjected to filtration. The filtration can be carried out utilizing one or more filtration steps. The filters utilized to carry out the filtration can have the capability to remove particles having a size in the range of about 0.1 $\mu$ to about 1.0$\mu$. According to one embodiment, four filtration steps are utilized to sequentially filter the solution with membrane filters of about 0.2 $\mu$ and about 0.1$\mu$. According to this embodiment, the solution is sequentially filtered through three filters having a porosity of about 0.1$\mu$. The solution typically is filtered into a sterile bulk container. Typically, the filtration is carried out in aseptic conditions.

The solution can then be filtered again. The filtering can be carried out as the final product is introduced into a container for the final product, in other words, a container that the product will be made available to customers in. Therefore, the filtering is typically carried out as point-of-fill filtration. The filtration can be carried out utilizing one or more filtration steps. The filters utilized to carry out the filtration can have the capability to remove particles in the range of about 0.2 $\mu$ to about 1.0$\mu$. According to one embodiment, two filtration steps are utilized to sequentially filter the solution with membrane filters of about 0.2$\mu$). According to this embodiment, the solution is filtered sequentially through two 0.2 $\mu$ filters. After the final filtration, the product is ready to package for shipment. The process as described above produces a final yield of about 80 to about 120 milliliters from about 1 liter of starting material serum.

This recovered purified lipoprotein/cholesterol complex is not pure cholesterol, but can be mixed with minor amounts of other materials, which passed through the production process. Along these lines, the complex typically is an aqueous mixture of cholesterol, phopholipids, and fatty acids. The resulting mixture has been found to be quite useful as a cell culture media supplement.

Example 2
Base Inactivation of Prion Infected Lipoprotein

Bovine serum starting material is maintained at a temperature of about 2° C. to about 15° C. The serum is filtered through 5 $\mu$ and 1 $\mu$ filters. The filtered serum is maintained at a temperature of about 2° C. to about 15° C.

Next, the filtered serum is subjected to an adsorption process. The adsorption process begins by adding sodium citrate to the filtered serum in an amount of about 12.8 to about 16.5 g of sodium citrate for each liter of filtered serum. The target amount of sodium citrate is about 14.7 g per liter of filtered serum. After adding the sodium citrate, the solution of filtered serum and sodium citrate are mixed. The mixing can be carried out for about 30 minutes.

Then, the adsorption process involves adding polyethyleneglycol (PEG) is added to the solution of filtered serum and sodium citrate. As discussed above, PEG having a range of molecular weights can be utilized. According to one example, PEG having an average molecular weight of about 3350 is utilized. However, PEG having greater or lesser molecular weights can also be utilized. Along these lines, PEG having an average molecular weight of about 6000 could be utilized. One of ordinary skill in the art, once aware of the disclosure contained herein would be able to determine the molecular weight of PEG to utilized with out undue experimentation based at least in part upon a known relationship between the ability of PEG to precipitate proteins being inversely proportional to the molecular weight of the PEG.

In this example, about 13.8 to about 15.6 grams of PEG 3350, available from Union Carbide, are added for each liter of serum and sodium citrate. The target amount is about 14.7 grams per liter. After adding the PEG, the solution is mixed. The mixing can be carried out for about 30 minutes.

After adding the PEG, the adsorption process includes adjusting the pH of the solution to an acidic level. The solution can be adjusted to a pH of about 5.85 to about 6.15. The acidification can be carried out utilizing 1N HCl.

Next in the adsorption process, the adsorbent is added to the solution. The amount of the adsorbent can depend upon its nature. In this example, a silica adsorbent is utilized. In particular, SIPERNAT 50, available from DeGussa, is utilized in an amount of about 18 g to about 22 g per liter of acidified serum. The target is about 20 g per liter of acidified serum. After adding the adsorbent, the solution is mixed. The mixing can be carried out for about 30 minutes.

After adding the adsorbent, the adsorption process includes adjusting the pH of the solution to an acidic level. The solution can be adjusted to a pH of about 5.85 to about 6.15. The acidification can be carried out utilizing 1N HCl. The solution can then be mixed. The mixing can be carried out for about 4 hours.

In the adsorption process, after adjusting the pH, about 31 g to about 35 g of FW-40 filteraid, available from Eagle-Picher, per liter of serum can be added to the pH-adjusted solution to aid in filtration. The target amount is about 33 g per liter of serum.

After adding the Filteraid, the solution can be mixed. The mixing can be carried out for about 30 minutes. After mixing, the solution can be maintained at a temperature below room temperature until filtering can be carried out. The solution can be maintained at a temperature of about 2° C. to below about 15° C.

The filtering can be carried out by filtering the suspension including the serum and adsorbent through a filter press to isolate a complex of the adsorbent and lipoproteins from the serum.

After filtration, the isolated complex of the adsorbent and lipoproteins is washed. The washing can be carried out in one or more washing steps. According to this particular example, two washing steps are utilized. The first washing step can be carried out with about 2.2 liters of 0.15 M sodium chloride/0.02M sodium phosphate at a pH of about 7 for each liter of starting serum. The second washing step can be the adsorbent and lipoprotein complex with about 4.4 liters of 0.02 M sodium phosphate at a pH of about 7 for each liter of starting serum.

After washing, the lipoproteins are recovered from the adsorbent and lipoprotein complex. The recovery can be carried out by eluting the washing adsorbent and lipoprotein complex with 0.6 liters of 0.3 M sodium carbonate at a pH of about 10.4 to about 10.6 for each liter of starting serum. The eluted solution can be maintained at a temperature of about 20° C. to about 27° C. and a pH of about 10.4 to about 10.6 by adding 1 N NaOH as needed.

At this point, a solution containing the lipoproteins can be filtered. The filtration can be carried out in at least one filtration step. In this example, the solution is filtered through approximately 1 $\mu$ and 0.45 $\mu$ filters.

At this point the elevated pH exposure step can be carried out. In this example, the pH is adjusted to about 12.0 to about 12.2 and held at that pH for about 8 hours at a temperature of about 18° C. to about 22° C.

After the pH is adjusted and held at the desired pH for a desired period of time, according to this example, the pH of the solution is adjusted to about 7.5 to about 8.5. According to this example, the pH is adjusted using 1 N HCl.

After adjusting the pH, the solution can be concentrated by ultrafiltration to approximately 1500 mg/dL cholesterol. Then, the concentrated solution can be filtered with 10 volumes of water, the volumes of water, for example, reverse osmosis (RO) water, being equivalent to the volume of concentrated solution. During the ultrafiltration process, the temperature of the solution can be maintained at about 20° C. to about 28° C.

After the ultrafiltration, the pH of the resulting solution can be adjusted to a slightly basic value. According to this example, the pH is adjusted to a value of between about 8.1 and about 8.2. Depending upon the starting pH of the solution, the pH can be adjusted up or down utilizing 1N NaOH or 1N HCl, respectively.

After adjusting the pH, the solution can be filtered. The filtration in this example is carried out in two steps. The first step is carried out utilizing a 0.65 $\mu$ membrane filter; the second step is carried out utilizing a 0.2 $\mu$ membrane filter.

After this filtration step, the solution including the lipoproteins is subjected to the heat treatment. To being the heat treatment step according to this example, the solution is heated typically from ambient temperature to a temperature of about 80° C. ± about 2° C. Upon the solution reaching about 80° C., the solution is maintained at the temperature for about 1 hour. After remaining at about 80° C. for about 1 hour to about 2 hour, the solution is permitted to cool to a temperature of about 67° C. ± about 1° C. After reaching about 67° C., the solution is maintained at a temperature of at least about 65° C. for at least about 3 hours. This 3 hour time includes the time above about 65° C. from the initial time period in which the solution is held at about 80° C. ± about 2° C. After the approximately 3 hour time period at which the solution is maintained at greater than about 65° C., the solution can be cooled to about 60° C. ± about 2° C. Upon achieving a temperature of about 60° C. ± about 2° C., the solution is maintained at a temperature of about 60° C. ± about 2° C. for about 10 hours. After being maintained at a temperature of about 60° C. ± about 2° C. for about 10 hours, the solution is cooled to about 20° C. to about 25° C. over a period of time of about 1 hour. In other words, the solution is cooled to ambient temperature. Upon achieving ambient temperature, the tank that the solution is contained in is cooled to about 2° C. to about 15° C. The heat treatment is thus concluded.

The solution is then filtered. According to this example, the filtration is carried out in four steps through four successively smaller filters. The solution is filtered through membrane filters of 0.65$\mu$, 0.45$\mu$, 0.2$\mu$, and 0.1$\mu$.

After filtration, the final cholesterol and pH adjustments are made. The pH of the solution is adjusted to about 7.9 to about 8.3 using 1 N HCl or 1 N NaOH, depending upon the starting pH of the solution. The cholesterol is adjusted to a concentration of about 1,020 mg/dL. According to this example, the cholesterol adjustment is made by adding water, such as reverse osmosis water (RO water), to the solution.

Subsequent to the pH and cholesterol adjustments, the solution is filtered again. According to this example, the filtration is carried out as follows. Four filter housings are prepared in series. The first housing will contain about 0.2 $\mu$filter media and the following three housings will be equipped with 0.1 $\mu$filter media. The first three housings are rinsed-in with RO water for about five minutes. During the rinsing, any air present in the filter housings is removed and clamps present in the housings are tightened. The last filter housing is connected to a sealed, pre-sterilized bulk vessel. The last filter housing is steamed in place at a temperature of about 133° C. to about 145° C. for a minimum of about 20 minutes and a maximum of about 30 minutes. After preparing the filter system, the solution is fed through the final filter system into the pre-sterilized bulk vessel.

After the final filtration, the solution is solution is fed from the pre-sterilized bulk vessel into pre-sterilized containers. The solution is once again filtered as it is fed into the pre-sterilized containers after passing sequentially through two filters having a porosity of about 0.2$\mu$.

This product material can be used in the same manner as that described above in Example 1. As described above, the process according to the present invention reduces, eliminates and/or inactivates transmissible spongiform encephalopathy agent that can be present in portions of a starting material to provide a growth supplement devoid or significantly devoid of the agent or at least devoid of infectious levels or active forms of the agent. To demonstrate these properties of the present invention, tests were carried out by treating a solution, or spiking material, which was exposed to a transmissible spongiform encephalopothy agent, to the alkaline treatment according to the present invention. The titer of the scrapie agent present in the output samples was assayed by titration in male Golden Syrian hamsters placed on test for up to 17 months. The results of the tests indicate that the process according to the present invention can successfully reduce, eliminate and/or inactivate infectious levels of transmissible spongiform encephalopothy agent present in a starting material from which a growth supplement is prepared.

In the discussion of the study, the following terms have the following meanings:

| | |
|---|---|
| CL = | 95% Confidence Limit |
| Initial Load = | Amount of scrapie in test article samples prior to treatment |
| $ID_{50}$ = | 50 percent infectivity |
| Output Load = | Amount of scrapie in test article sample after treatment |
| Output Sample = | Sample after treatment |
| Prove spike = | Test article sample after addition of test material and prior to inactivation |
| Sample ID = | Sample identification |
| TSE = | Transmissible Spongiform Encephalopathies |

The transmissible spongiform encephalopothy agent utilized in the study was a scrapie agent. In particular, the spiking preparation utilized in the study was the hamster adapted (263K) strain of Scrapie agent licensed from the Institute of Animal Health (IAH), Edinburgh, Scotland. The original material was a pool of scrapie infected brain from Cheviot sheep which was injected into goats. After eight passages in goats, a passage was made through mice, which were homozygous for the $s^7$ allele of the Sinc gene. This material was passaged through rats and through four passages in hamsters. Five additional cloning passages in hamsters were carried out. Several additional hamster passages were performed prior to utilization of the material in the study.

The in vivo evaluation of the process according to the present invention included quantitative titrations of the spiking material at dilutions of $10^{-4}$ through $10^{-10}$ using 6 hamsters per dilution, qualitative demonstration of the load activity in an undiluted state, quantitative titrations of the output samples at dilutions of neat through $10^{-7}$ using 6 hamsters per dilution, and testing of a prove spike sample in an undiluted state in 6 hamsters.

Twelve uninoculated control animals and twelve sham inoculated control animals from the same shipment of animals, maintained under the same husbandry conditions, and in the same location as the inoculated animals were included in the study. Hamsters were observed for clinical disease signs and sacrificed when moribund.

The spiking material for the study was prepared as a supernatant of a 10% hamster brain homogenate. Scrapie infected hamster brains (263K strain) were homogenized using a sterile glass tissue grinder. A 10% w/v suspension was prepared using Hank's Balanced Salt Solution (HBSS). The homogenate was clarified at 1,000 rpm for 10 minutes.

The Alkaline Treatment for Runs 1 and 2 was performed at room temperature. The initial pH of the load material was pH 10.48. A 27 mL aliquot of the neutral load material was equilibrated for 15 minutes at room temperature. The 27 mL aliquot of neutral load material was spiked with 3 mL of scrapie agent. A 5 mL sample was immediately collected. This was the prove spike sample. The pH of the remaining 25 mL sample was increased to pH 12.1±1 by the addition of 1.3 mL of 1N NaOH. A 5 mL sample was collected at each of the following timepoints: T=0 minutes, T=2 hours, T=4 hours, T=6 hours and T=8 hours. Each timepoint sample was immediately neutralized to pH 7.5–8.0 upon collection. The neutralized samples were immediately stored on dry ice.

Ten-fold dilutions of the spiking material samples (10% brain homogenate) were prepared from undilute through $10^{-10}$ using sterile HBSS. Ten-fold dilutions of the process samples were prepared from undilute through a dilution of $10^{-7}$ using sterile HBSS. Prove spike samples were tested at undilute.

Each animal cage was assigned a number and labelled with the study number, test article identification, cage/group number and date of administration. All animals were randomized. AVID implants were inserted into each hamster and the animals were ear punched. The animals were housed in groups of 6 animals per cage, according to inoculum type.

Various treatments were administered to the animals. Working with one cage a time, using aseptic technique, and working in a biological safety cabinet, 0.05 mL of the appropriate treatment was administered intracranially (IC) to hamsters anesthetized with metofane (Source: Mallinckrodt).

All animals were fed Agway (autoclavable Prolab) diet ad libitum. Water was supplied via apples or autoclaved water in water bottles. Bed-O-Cobs bedding was utilized. Animal facilities were utilized that are accredited by the Association for Assessment and Accreditation of Laboratory Animal Care, International.

All treated animals and the untreated control animals were observed every working day for signs of disease and the observations recorded for the entire observation period. Animals were observed for death on the weekends. Animals found dead on weekends were identified and sent for necropsy. Animals that died less than 24 hours post-inoculation were not sent for necropsy.

Animals were observed for clinical signs of scrapie infection. Clinical signs of the terminal disease stage generally proceed from abnormality of gait and tremors, to severe ataxia and sometimes urinary incontinence evidenced by a wet anogenital area. Animals at the terminal disease stage were sacrificed and sent for harvest of the brain. Histopathological examination of the brains of all dead or sacrificed animals was performed to confirm clinical diagnosis. Animals that died or appeared moribund without exhibiting clinical signs of scrapie infection were sent for a complete necropsy.

At the appropriate time point, hamsters that exhibited clinical signs of scrapie were sacrificed by $CO_2$ asphyxiation, and the brains removed, fixed, treated with formic acid and trimmed. The brains were temporarily placed in labelled cassettes. The tissues were processed through paraffin cut at 5–6μ, stained with hematoxylin and eosin (H&E) and evaluated microscopically. In the instances where animals died or were sacrificed without clinical signs of scrapie infection, a complete necropsy was performed. All harvested tissues were fixed and reserved for processing, and examination if necessary. Brain tissues were processed and examined as described above. Some histopathological examination of tissues other than brains was performed.

The hamsters identified as having scrapie consistent brain lesions had vacuolization of the brain which was considered to be consistent with published criteria (Fraser H. and Dickinson A. G., J. Comp. Path. 78, 301–311, 1968). The specific areas of the brain examined, when present, included medulla, cerebellum, thalamus, hippocampus and cerebral cortex. Vacuolization of the neuropil was subjectively graded minimal for those areas of the brain having a few small discrete vacuoles, to mark when vacuoles were numerous, variable in size, and confluent. Vacuolization denoted as mild or moderate represents intermediate levels of severity. The brains of some animals that were found dead had autolytic artifacts, which included vacuolization that interfered with the interpretation and diagnosis of scrapie.

Tables 4 and 5 below provide results of treatment of hamsters with scrapie infected brain material that had not been subjected to the alkaline treatment according to the present invention. The titer and 95% Confidence Limits were calculated. The formula for the final titer calculation of $ID_{50}$ is based on the Karber method disclosed by Lennette, *General Principles Underlying Laboratory Diagnosis of Viral and Rickettsial Infections*, Eds Lennette et al. *Diagnostic Procedures for Viral and Rickettsial Diseases*, 3d ed., 1964, the entire contents of the disclosure of which are hereby incorporated by reference.

TABLE 4

Sample ID: I. 10% Brain Homogenate-Run 1, AA01KW-1
Inoculum Vol (mL): 0.050

| $Log_{10}$ Dilution Factor | NUMBER WITH SCRAPIE Consistent Pathology | Number Evaluated |
|---|---|---|
| 4.0 | 6 | 6 |
| 5.0 | 6 | 6 |
| 6.0 | 4 | 6 |
| 7.0 | 1 | 6 |
| 8.0 | 1 | 6 |
| 9.0 | 0 | 6 |
| 10.0 | 0 | 6 |

$Log_{10}$ $ID_{50}$/mL: 7.80
95% Confidence Limit: 0.62

TABLE 5

Sample ID: II. 10% Brain Homogenate-Run 2, AA01KW-1
Inoculum Vol (mL): 0.050

| $Log_{10}$ Dilution Factor | NUMBER WITH SCRAPIE Consistent Pathology | Number Evaluated |
|---|---|---|
| 4.0 | 6 | 6 |
| 5.0 | 6 | 6 |
| 6.0 | 6 | 6 |
| 7.0 | 3 | 6 |
| 8.0 | 1 | 6 |

TABLE 5-continued

| | | |
|---|---|---|
| 9.0 | 0 | 4[a] |
| 10.0 | 0 | 6 |

$Log_{10}$ $ID_{50}$/mL: 8.47
95% Confidence Limit: 0.55
[a]Autolysis precluded evaluation of two animals Tables 6 and 7 below provide results for treatment of hamsters with scrapie infected brain material that was subjected to the alkaline treatment according to the present invention for 0 hours. In other words, the alkaline material was added to the sample and immediately the pH was adjusted down as described above. The titer and 95% Confidence Limits were again calculated. The formula for the final titer calculation of $ID_{50}$ was again based on the Karber method.

TABLE 6

Sample ID: III. Alkaline Treatment-Run 1, T = 0, AA01KW-5
Inoculum Vol (mL): 0.050

| $Log_{10}$ Dilution Factor | NUMBER WITH SCRAPIE Consistent Pathology | Number Evaluated |
|---|---|---|
| 0.0 | 5 | 5[a] |
| 1.0 | 4 | 5[a] |
| 2.0 | 6 | 6 |
| 3.0 | 5 | 6 |
| 4.0 | 5 | 6 |
| 5.0 | 3 | 6 |
| 6.0 | 1 | 6 |
| 7.0 | 0 | 6 |

$Log_{10}$ $ID_{50}$/mL: 5.97
95% Confidence Limit: 0.79
[a]Autolysis precluded evaluation of one animal.

TABLE 7

Sample ID: IV. Alkaline Treatment-Run 2, T = 0 AA01KW-11
Inoculum Vol (mL): 0.050

| $Log_{10}$ Dilution Factor | NUMBER WITH SCRAFIE Consistent Pathology | Number Evaluated |
|---|---|---|
| 0.0 | 6 | 6 |
| 1.0 | 6 | 6 |
| 2.0 | 6 | 6 |
| 3.0 | 6 | 6 |
| 4.0 | 4 | 5[a] |
| 5.0 | 2 | 6 |
| 6.0 | 1 | 6 |
| 7.0 | 0 | 6 |

$Log_{10}$ $ID_{50}$/mL: 6.13
95% Confidence Limit: 0.62
[a]Autolysis precluded evaluation of one animal.

Tables 8 and 9 below provide results for treatment of hamsters with scrapie infected brain material that was subjected to the alkaline treatment according to the present invention for 2 hours. The titer and 95% Confidence Limits were again calculated. The formula for the final titer calculation of $ID_{50}$ was again based on the Karber method.

TABLE 8

Sample ID: V. Alkaline Treatment-Run 1, T = 2H, AA01KW-6
Inoculum Vol (mL): 0.050

| $Log_{10}$ Dilution Factor | NUMBER WITH SCRAPIE Consistent Pathology | Number Evaluated |
|---|---|---|
| 0.0 | 5 | 5[a] |
| 1.0 | 5 | 6 |

TABLE 8-continued

| | | |
|---|---|---|
| 2.0 | 3 | 5[b] |
| 3.0 | 3 | 6 |
| 4.0 | 0 | 6 |
| 5.0 | 0 | 6 |
| 6.0 | 0 | 6 |
| 7.0 | 0 | 6 |

$Log_{10}$ $ID_{50}$/mL: 3.80
95% Confidence Limit: 0.69
[a]Autolysis precluded evaluation of one animal.
[b]Tissues from one animal were unavailable for evaluation.

TABLE 9

| Sample ID: | VI. Alkaline Treatment-Run 2, T = 2H, AA01KW-12 | |
|---|---|---|
| Inoculum Vol (mL): | 0.050 | |

| $Log_{10}$ Dilution Factor | NUMBER WITH SCRAPIE Consistent Pathology | Number Evaluated |
|---|---|---|
| 0.0 | 5 | 6 |
| 1.0 | 6 | 6 |
| 2.0 | 5 | 6 |
| 3.0 | 0 | 5[a] |
| 4.0 | 0 | 6 |
| 5.0 | 0 | 5[a] |
| 6.0 | 0 | 6 |
| 7.0 | 0 | 6 |

$Log_{10}$ $ID_{50}$/mL: 3.46
95% Confidence Limit: 0.40
[a]Autolysis precluded evaluation of one animal.

Tables 10 and 11 below provide results for treatment of hamsters with scrapie infected brain material that was subjected to the alkaline treatment according to the present invention for 4 hours. The titer and 95% Confidence Limits were again calculated. The formula for the final titer calculation of $ID_{50}$ was again based on the Karber method.

TABLE 10

| Sample ID: | VII. Alkaline Treatment-Run 1, T = 4H, AA01KW-7 | |
|---|---|---|
| Inoculum Vol (mL): | 0.050 | |

| $Log_{10}$ Dilution Factor | NUMBER WITH SCRAPIE Consistent Pathology | Number Evaluated |
|---|---|---|
| 0.0 | 5 | 5[a] |
| 1.0 | 6 | 6 |
| 2.0 | 4 | 5[a] |
| 3.0 | 0 | 6 |
| 4.0 | 0 | 6 |
| 5.0 | 0 | 6 |
| 6.0 | 0 | 6 |
| 7.0 | 0 | 5[a] |

$Log_{10}$ $ID_{50}$/mL: 3.63
95% Confidence Limit: 0.33
[a]Autolysis precluded evaluation of one animal.

TABLE 11

| Sample ID: | VIII. Alkaline Treatment-Run 2, T = 4H, AA01KW-13 | |
|---|---|---|
| Inoculum Vol (mL): | 0.050 | |

| $Log_{10}$ Dilution Factor | NUMBER WITH SCRAPIE Consistent Pathology | Number Evaluated |
|---|---|---|
| 0.0 | 6 | 6 |
| 1.0 | 4 | 6 |
| 2.0 | 6 | 6 |
| 3.0 | 2 | 6 |
| 4.0 | 0 | 6 |
| 5.0 | 0 | 6 |
| 6.0 | 0 | 6 |
| 7.0 | 0 | 6 |

$Log_{10}$ $ID_{50}$/mL: 3.80
95% Confidence Limit: 0.58

Tables 12 and 13 below provide results for treatment of hamsters with scrapie infected brain material that was subjected to the alkaline treatment according to the present invention for 6 hours. The titer and 95% Confidence Limits were again calculated. The formula for the final titer calculation Of $ID_{50}$ was again based on the Karber method.

TABLE 12

| Sample ID: | IX. Alkaline Treatment-Run 1, T = 6H, AA01KW-8 | |
|---|---|---|
| Inoculum Vol (mL): | 0.050 | |

| $Log_{10}$ Dilution Factor | NUMBER WITH SCRAPIE Consistent Pathology | Number Evaluated |
|---|---|---|
| 0.0 | 6 | 6 |
| 1.0 | 4 | 4[a] |
| 2.0 | 0 | 6 |
| 3.0 | 0 | 5[b] |
| 4.0 | 0 | 6 |
| 5.0 | 0 | 5[b] |
| 6.0 | 0 | 5[b] |
| 7.0 | 0 | 6 |

$Log_{10}$ $ID_{50}$/mL: 2.80
95% Confidence Limit: 0.00
[a]Autolysis precluded evaluation of two animals.
[b]Autolysis precluded evaluation of one animal.

TABLE 13

| Sample ID: | X. Alkaline Treatment-Run 2, T = 6H, AA01KW-14 | |
|---|---|---|
| Inoculum Vol (mL): | 0.050 | |

| $Log_{10}$ Dilution Factor | NUMBER WITH SCRAPIE Consistent Pathology | Number Evaluated |
|---|---|---|
| 0.0 | 5 | 6 |
| 1.0 | 5 | 6 |
| 2.0 | 3 | 6 |
| 3.0 | 0 | 5[a] |
| 4.0 | 0 | 6 |
| 5.0 | 0 | 6 |
| 6.0 | 0 | 6 |
| 7.0 | 0 | 5[a] |

$Log_{10}$ $ID_{50}$/mL: 2.96
95% Confidence Limit: 0.59
[a]Autolysis precluded evaluation of one animal.

Tables 14 and 15 below provide results for treatment of hamsters with scrapie infected brain material that was subjected to the alkaline treatment according to the present invention for 8 hours. The titer and 95% Confidence Limits were again calculated. The formula for the final titer calculation of $ID_{50}$ was again based on the Karber method.

TABLE 14

| Sample ID: | XI. Alkaline Treatment-Run 1, T = 8H, AA01KW-9 | |
|---|---|---|
| Inoculum Vol (mL): | 0.050 | |

| $Log_{10}$ Dilution Factor | NUMBER WITH SCRAPIE Consistent Pathology | Number Evaluated |
|---|---|---|
| 0.0 | 6 | 6 |
| 1.0 | 5 | 5[a] |
| 2.0 | 2 | 5[a] |

TABLE 14-continued

| | | |
|---|---|---|
| 3.0 | 1 | 5[a] |
| 4.0 | 0 | 6 |
| 5.0 | 0 | 6 |
| 6.0 | 0 | 6 |
| 7.0 | 0 | 6 |

$Log_{10}$ $ID_{50}$/mL: 3.3
95% Confidence Limit: 0.53
[a]Autolysis precluded evaluation of one animal.

TABLE 15

| | |
|---|---|
| Sample ID: | XII. Alkaline Treatment-Run 2, T = 8H, AA01KW-15 |
| Inoculum Vol (mL): | 0.050 |

| $Log_{10}$ Dilution Factor | NUMBER WITH SCRAPIE Consistent Pathology | Number Evaluated |
|---|---|---|
| 0.0 | 6 | 6 |
| 1.0 | 6 | 6 |
| 2.0 | 4 | 6 |
| 3.0 | 0 | 5[a] |
| 4.0 | 0 | 6 |
| 5.0 | 0 | 4[b] |
| 6.0 | 0 | 6 |
| 7.0 | 0 | 6 |

$Log_{10}$ $ID_{50}$/mL: 3.47
95% Confidence Limit: 0.41
[a]Tissues from one animal were unavailable for evaluation.
[b]Autolysis precluded evaluation of two animals.

The scrapie reduction factor in the study is the log10 of the ratio of the input scrapie load and the output scrapie load. If $v_1$ and $t_1$ represent the input volume (mL) and scrapie agent concentration ($ID_{50}$), respectively; and if $v_2$ and $t_2$ represent the output volume and scrapie agent concentration, respectively; then $v_1t_1$ is the input scrapie load and $v_2t_2$ is the output scrapie load. The scrapie reduction factor, r, is given by the expression:

$$r = \log 10((v_1 t_1)/(v_2 t_2))$$

Due to the fact that immediate inactivation was evidenced in the T=0 sample of Run 1 and Run 2, the load titer used to calculate the reduction factors was a theoretical load titer. This was calculated using the results from the homogenate spiking material (AA01KW-1 Run 1 and Run 2) adjusted for the spiking dilution (1:10). Table 16 provides a summary of the results for the study.

TABLE 16

| Sample | Titer ± 95% CL ($Log_{10}$ $ID_{50}$/mL) | Volume (mL) | Volume Correction (mL)[1] | Scrapie Agent Load ($Log_{10}$ $ID_{50}$) |
|---|---|---|---|---|
| Uninoculated Control Sham Inoculated Control | — | — | — | — |
| Scrapie Spike 10% Brain Homogenate Run 1 - AA01KW-1 | 7.80 ± 0.62 | — | — | — |
| Scrapie Spike 19% Brain Homogenate Run 2 - AA01KW-1 | 8.47 ± 0.55 | — | — | — |
| Scrapie Spike Theoretical Load Run 1 - AA01KW-1 | 6.80 ± 0.62[2] | 25 | — | 8.20 |
| Scrapie Spike Theoretical Load Run 2 - AA01KW-1 | 7.47 ± 0.55[2] | 25 | — | 8.87 |
| Alkaline Treatment Run 1 - T = 0, AA01KW-5 | 5.97 ± 0.79 | 26.3 | 1.21 | 7.47 |
| Alkaline Treatment Run 1 - T = 2H, AA01KW-6 | 3.80 ± 0.69 | 26.3 | 1.21 | 5.30 |
| Alkaline Treatment Run 1 - T = 4H, AA01KW-7 | 3.63 ± 0.33 | 26.3 | 1.21 | 5.13 |
| Alkaline Treatment Run 1 - T = 6H, AA01KW-8 | 2.80 | 26.3 | 1.21 | 4.3 |
| Alkaline Treatment Run 1 - T = 8H, AA01KW-9 | 3.3 ± 0.53 | 26.3 | 1.21 | 4.8 |
| Alkaline Treatment Run 2 - T = 0, AA01KW-11 | 6.13 ± 0.62 | 26.3 | 1.21 | 7.63 |
| Alkaline Treatment Run 2 - T = 2H, AA01KW-12 | 3.46 ± 0.40 | 26.3 | 1.21 | 4.96 |
| Alkaline Treatment Run 2 - T = 4H, AA01KW-13 | 3.80 ± 0.58 | 26.3 | 1.21 | 5.3 |
| Alkaline Treatment Run 2 - T = 6H, AA01KW-14 | 2.96 ± 0.59 | 26.3 | 1.21 | 4.46 |
| Alkaline Treatment Run 2 - T = 8H, AA01KW-15 | 3.47 ± 0.41 | 26.3 | 1.21 | 4.97 |

[1]Volume correction accounts for the neutralization of samples prior to titration. Viral load = $log_{10}$ (volume correction × sample volume) + $log_{10}$ titer.
[2]Titer adjusted for 1:10 spiking dilution.

As shown in Table 17, the alkaline treatment according to the present invention has a tremendous effect on reducing the amount of scrapie agent. This reduction can be correlated to reduction in transmissible spongiform encephalopathy agent in a cholesterol-rich fraction isolated and purified from mammalian blood plasma or serum.

TABLE 17

| | Reduction Factors | | |
|---|---|---|---|
| PROCESS STEP | Initial Load ($Log_{10}$ $ID_{50}$)* | Output Load ($Log_{10}$ $ID_{50}$) | Reduction ($Log_{10}$) |
| Alkaline Treatment Run 1 T = 8H | 8.20 | 4.80 | 3.40 |
| Alkaline Treatment Run 2 T = 8H | 8.87 | 4.97 | 3.90 |
| Average Log Reduction | | | 3.72 |

*Due to immediate inactivation evidenced in the T = 0 sample, the assay positive control titer, adjusted for the spiking dilution, was used as the theoretical load titer.

Example 3

Removal of Prions by Silica Adsorption of Lipoprotein

Lipoproteins are dissolved in an appropriate solvent, for example, a buffer, and filtered if desired to remove particulate. After optional filtration, the lipoproteins in the optionally filtered material are adsorbed onto an adsorbent. Any suitable adsorbent can be utilized. One example is silica-containing adsorbents. A silica adsorbent useful in this invention does not have a critical composition. Appropriate silica materials, as described in Example 2, are the microfine silica available under the trademark Cabosil from Cabot Corporation and AEROSIL and SIPERNAT, such as the powdered silica SIPERNAT 50, manufactured by DeGussa and available from Cary Co. The silica is added to the lipoprotein solution in an amount of about 1 to about 50 g/L, typically about 10 to about 20 g/L. The silica suspension is then mixed for about 3 to about 4 hours.

The adsorption can be carried out at a slightly acidic pH. The adsorption can be carried out at a pH of about 5 to about 8. Typically, the adsorption is carried out at a pH of about 5.8 to about 6.2. According to one example, the adsorption is carried out at a pH of about 6. Additionally, the adsorption can be carried out at a temperature of about 15° C. to about 30° C. for about 2 hours to about 24 hours. After adding the adsorbent(s), the solution can be mixed. According to one embodiment, the solution is mixed for about 30 to about 6 hours.

After adsorption, the lipoprotein-adsorbent complex can be isolated and remaining prion-containing solution discarded. The isolation can be carried out as a simple phase separation utilizing a filter press.

Subsequent to isolating the lipoprotein-adsorbent complex, occluded proteins or other undesired components can be removed from the lipoprotein-adsorbent complex. The removal can be carried out utilizing a high salt buffer wash. According to one example, this can be accomplished by washing the lipoprotein-adsorbent complex with an aqueous salt solution containing about 0.15 M sodium chloride. Other useful salts can include sodium acetate and/or sodium phosphate. The pH of the solution can also vary. Typically, the pH of the wash solution is about 6.9 to about 7.1. Similarly, the temperature that the wash is carried out at can vary. Typically, the temperature is about 2° C. to about 30° C. The salt solution is used in an amount about 120 liters for about each kilogram of the lipoprotein-adsorbent complex. Typically, the total volume of wash solution utilized could be about 12,000 liters to about 24,000 liters. According to one embodiment, two wash steps are carried out, each utilizing about 12,000 liters of wash solution. According to another embodiment, two wash steps could be carried out, each utilizing about 6,000 liters of solution. However, the volume could be more or less. The washing can be accomplished as a batch process or in a continuous washing process. According to one embodiment, the washing procedure is carried out at least two times as a batch process to remove unwanted contaminants. According to one particular embodiment, a first wash is carried out utilizing about 12,000 liters of a solution that contains about 8.3 to about 9.2 grams sodium chloride per liter and about 2.1 to about 2.9 grams sodium phosphate per liter at a pH of about 6.9 to about 7.1 and at a temperature of about 2° C. to about 30° C. This embodiment also includes carrying out a second washing step with about 12,000 liters of a solution that includes about 2.1 to about 2.9 grams sodium phosphate per liter at a pH of about 6.9 to about 7.1 at a temperature of about 2° C. to about 30° C. In embodiments that utilize a filter press to carry out the washing, the washing, whether a batch or continuous process, continues until reaching a target absorbance for the wash collection. According to one embodiment, the absorbance is less than about 0.1 at 280 nm. After washing the isolated the lipoprotein-adsorbent complex, the material utilized to remove the occluded proteins can be discarded.

The purified lipoproteins can then be recovered from the adsorbent. The recovery can be carried out at an elevated pH. According to one embodiment, the recovery is carried out at a pH of about 10.5. According to another embodiment, the recovery is carried out by passing a high pH buffered solution through the lipoprotein-adsorbent complex until cholesterol is substantially removed from the adsorbent. After recovering the purified lipoproteins, the adsorbent is discarded.

A solution containing the recovered lipoproteins can then be filtered. The filtration can be carried out utilizing one or more filtration steps. According to one embodiment, two filtration steps are utilized. A first filtration step utilizes filters having a nominal porosity of about $1\mu$. A second filtration step utilizes membrane filters having a porosity of about $0.45\mu$. In this and any of the filtration steps described herein, other filters can be utilized having different porosities as long as the porosity results in filtering particles of the desired size. Those of ordinary skill in the art would be able to determine suitable filter porosities without undue experimentation.

It is to be understood that the described invention is capable of use in various other combinations, modifications, and environments and is capable of changes or modifications within the scope of the inventive concept as expressed herein, commensurate with the above teachings, and/or the skill or knowledge of the relevant art. Accordingly, the description is not intended to limit the invention to the form disclosed herein. Also, it is intended that the appended claims be construed to include alternative embodiments.

We claim:

1. A process to inactivate prions in a purified lipoprotein material, extracted from blood plasma or serum of a prion infected animal in a manner that does not substantially adversely affect the biological activity of the lipoprotein material comprising contacting the lipoprotein material with a solution of base at a pH of between 10 and 13 for a sufficient time period to cause prion inactivation.

2. The process of claim 1, wherein the purified lipoprotein material is contacted with the solution of base at approximately room temperature.

3. The process of claim 1, wherein the base is sodium hydroxide.

4. The process of claim 1, wherein the base is potassium hydroxide.

5. The process of claim 1, wherein the base is hydroxide ion.

6. The process of claim 1, wherein the base is an ammonium ion or amine.

7. The process of claim 1, wherein the base is in a concentration of between 0.1 and 1N solution.

8. The process of claim 1, wherein the purified lipoprotein material is contacted with the base for a period of time of from initial contact up to 10 hours.

9. The process of claim 1, wherein the lipoprotein material is contacted with the base for at least 2 hours.

10. The process of claim 1, wherein the lipoprotein material is contacted with the base for at least 4 hours.

11. The process of claim 1, wherein the lipoprotein material is contacted with the base for at least 6 hours.

12. The process of claim 1, wherein the lipoprotein material is contacted with the base for at least 8 hours.

13. The process of claim 1, wherein the lipoprotein material is contacted with the base for at least 10 hours.

14. The process of claim 1, wherein the wherein the lipoprotein material is contacted at a pH of about 12 for about 8 hours.

15. The process of claim 1, wherein the lipoprotein material is contacted at a temperature between about 16° C. and about 24° C.

16. The process of claim 1, wherein the lipoprotein in the lipoprotein material is at a concentration between 10 and 3,500 mg/dL.

17. The process of claim 1, wherein the lipoprotein in the lipoprotein material is at a concentration between 50 and 500 mg/dL.

18. The process of claim 1, further comprising after contacting the lipoprotein material with a solution of base adjusting the pH to a neutral pH using a pH-adjusting agent that does not adversely affect the lipoprotein material.

19. The process of claim 1, wherein the purified lipoprotein material comprises lipoprotein material and solvent.

20. The process of claim 1, wherein the lipoprotein material is substantially pure lipoprotein.

21. The process of claim 1, wherein the lipoprotein is in a solvent selected from water, saline, and buffer.

22. The process of claim 1, wherein the purified lipoprotein material includes cholesterol.

23. The process of claim 1, wherein the purified lipoprotein material includes a lipid selected from the group consisting of a triglyceride, a fatty acid and a phospholipid.

24. A process for removing prions from a lipoprotein solution comprising contacting the solution with an adsorbant that binds more tightly to a lipoprotein than to a prion.

25. The process of claim 24, wherein the adsorbent contains silica.

26. The process of claim 25, wherein the lipoprotein is mixed with silica at a pH that does not cause the removal of the lipoprotein from the silica.

27. The process of claim 26, wherein the pH is between 6 and 8.

28. The process of claim 26, further comprising separating the lipoprotein bound to the silica-based adsorbent from absorbed serum or plasma in the lipoprotein solution by filtration, which results in a lipoprotein-silica complex.

29. The process of claim 28, further comprising substantially removing the lipoprotein from the silica.

30. The process of claim 29, wherein the lipoprotein is removed via an elevated pH.

31. The process of claim 29, wherein the lipoprotein is removed by passing a high pH buffered solution through the lipoprotein silica complex until the lipoprotein is removed from the silica.

32. The process of claim 24, wherein the lipoprotein contains cholesterol.

33. The process of claim 24, wherein the lipoprotein includes material selected from the group consisting of a triglyceride, a fatty acid and a phospholipid.

34. The process of claim 1, further comprising after contacting the lipoprotein material with a solution of base, adjusting the pH to between about pH 4 and 9 with a pH-adjusting agent that does not adversely affect the lipoprotein.

35. The process of claim 1, further comprising after contacting the lipoprotein material with a solution of base, adjusting the pH to between about pH 5.5 and about 6.5 with a pH-adjusting agent that does not adversely affect the lipoprotein.

36. The process of claim 1, further comprising after contacting the lipoprotein material with a solution of base, adjusting the pH to about 8.5 with a pH-adjusting agent that does not adversely affect the lipoprotein.

37. The process of claim 1 wherein the purified lipoprotein material constitutes up to 60, 70, 80 or 90 percent or higher by weight of the material being treated.

38. The process of claim 1 wherein the lipoprotein is in substantially pure form.

39. The process of claim 22 wherein the cholesterol is in substantially pure form.

40. A process to inactivate prions in a purified lipoprotein material, extracted from blood plasma or serum of prion infected material, in a manner that does not substantially adversely affect the biological activity of the lipoprotein material comprising contacting the lipoprotein material with a solution of base at a pH of between 10 and 13 for a sufficient time period to cause prion inactivation.

41. A process to inactivate prions in a purified lipoprotein material from a prion infected source in a manner that does not substantially adversely affect the biological activity of the lipoprotein material comprising contacting the lipoprotein material with a solution of base at a pH of between 10 and 13 for a sufficient time period to cause prion inactivation.

* * * * *